(12) United States Patent
Corriu et al.

(10) Patent No.: US 7,517,512 B2
(45) Date of Patent: Apr. 14, 2009

(54) MESOPOROUS ORGANIC-INORGANIC HYBRID MATERIALS FOR SEPARATING GASES

(75) Inventors: Robert Corriu, Montpellier (FR); Ahmad Mehdi, Montpellier (FR); Catherine Reye, Montpellier (FR); Henry Ledon, Versailles (FR); Roger Guilard, Fontaine les Dijon (FR); Stéphane Brandes, Dijon (FR); Chloé Thieuleux, Calais (FR)

(73) Assignee: Centre National de la Recherche-Scientifique, Paris (FR)

( * ) Notice: Subject to any disclaimer, the term of this patent is extended or adjusted under 35 U.S.C. 154(b) by 0 days.

(21) Appl. No.: 12/043,486

(22) Filed: Mar. 6, 2008

(65) Prior Publication Data

US 2008/0152561 A1    Jun. 26, 2008

Related U.S. Application Data

(63) Continuation of application No. 10/472,301, filed as application No. PCT/FR02/00986 on Mar. 21, 2002, now Pat. No. 7,452,845.

(30) Foreign Application Priority Data

Mar. 21, 2001   (FR) .................................. 01 03802

(51) Int. Cl.
*B01D 53/86* (2006.01)
(52) U.S. Cl. ....................... 423/219; 502/439
(58) Field of Classification Search ............. 423/219; 502/400, 439
See application file for complete search history.

(56) References Cited

OTHER PUBLICATIONS

International Search Report corresponding to International Application No. PCT/FR02/00986.
English translation of International Search Report corresponding to International Application No. PCT/FR02/00986.
International Preliminary Examination Report corresponding to International Application No. PCT/FR02/00986.
English translation of International Preliminary Examination Report corresponding to International Application No. PCT/FR02/00986.
6001 Chemical Abstracts, Columbus, Ohio, US—vol. 131, No. 6, dated Sep. 8, 1999 XP-002186598 (1 Page) Authors: Corriu, R.J., Mehdi, A., and Reye, C.
6001 Chemical Abstracts, Columbus, Ohio, US—vol. 132, No. 17, dated Apr. 24, 2000 XP-002186597 (1 Page) Authors: Graham, U.M. and Thomas, G.

*Primary Examiner*—Edward M Johnson
(74) *Attorney, Agent, or Firm*—Husch Blackwell Sanders Welsh & Katz

(57) ABSTRACT

The invention concerns a method for preparing organic-inorganic hybrid materials with controlled porosity and functionality comprising hydrolysis and condensation polymerization of a compound of formula (I): $Z-R_1-Si(OR)(OR')(OR'')$, with an alkaline or alkaline-earth silicate in a mol ratio of (I)/(silicate)=1:9, in the presence of a non-ionic surfactant, to form a mesoporous silica represented by $Z-R_1-SiO_{1.5}$ 9 $SiO_2$, whereon is then anchored an organic compound, represented by $(\Delta)N-H$, comprising a $-NH-$ group capable of reacting with Z, to form a functionalized mesoporous silica represented by $(\Delta)N-R-SiO_{1.5}$ 9 $SiO_2$, which is optionally complexed with a metallic cation to form an organometallic complex. The invention also concerns the use of these materials to separate gases.

6 Claims, 1 Drawing Sheet

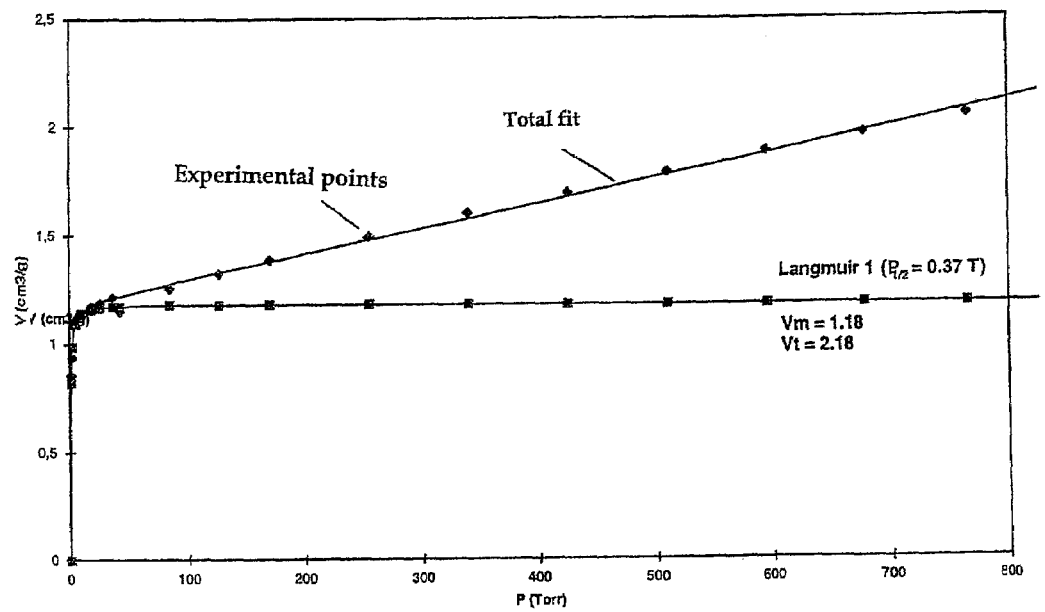
Fig. 1 Isotherm of adsorption of $O_2$ on the material $M_B$ (7-Cu) (1$^{st}$ cycle)
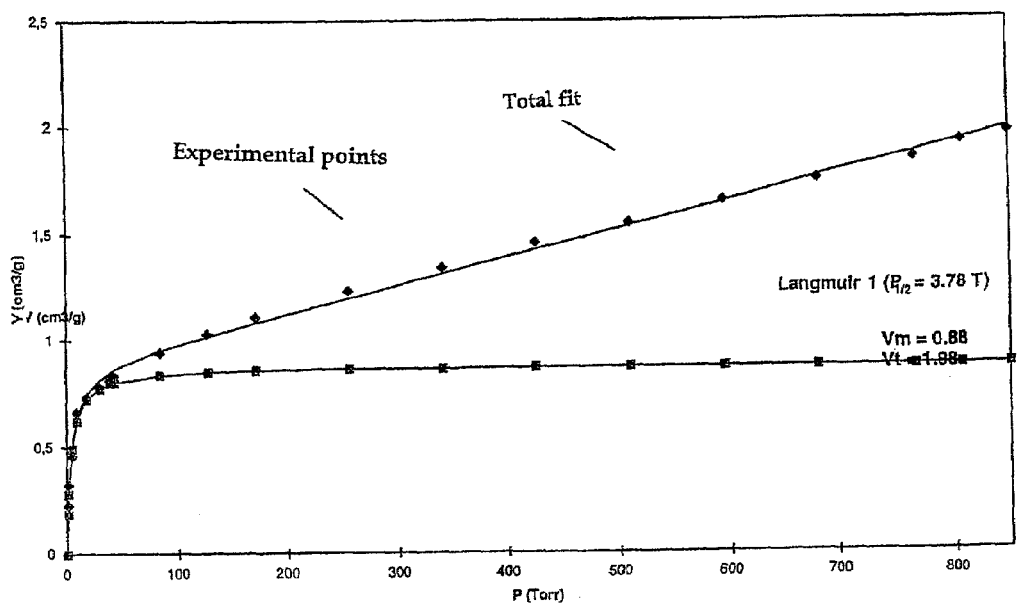
Fig. 2 Isotherm of adsorption of $O_2$ on the material $M_B$ (9-Cu) (1$^{st}$ cycle)

MESOPOROUS ORGANIC-INORGANIC HYBRID MATERIALS FOR SEPARATING GASES

CROSS-REFERENCE TO RELATED APPLICATIONS

This application is a continuation of U.S. application Ser. No. 10/472,301, which is the National State of International Application No. PCT/FR02/00986, filed on Mar. 21, 2002.

BACKGROUND OF THE INVENTION

The invention relates to the preparation of mesoporous organic-inorganic hybrid materials which may be used in the purification of gases.

Current separation techniques (cryogenic distillation or adsorption on zeolites) and techniques for the purification of industrial gases (cryogenic distillation or catalysis) are not always optimized, either in economic terms (cryogenics in the case of small quantities) or in terms of gas purity (the oxygen obtained by adsorption contains 5% of argon, for example). Many studies have shown that gases such as oxygen, hydrogen or carbon monoxide react selectively and reversibly with transition metal complexes. Thus, cobalt(II) complexes of cyclam or of cyclene are known to coordinate dioxygen strongly in solution (R. Machida, E. Kimura, M. Kodama, Inorg. Chem., 1983, 22, 2055).

However, the lifetime of oxygen-containing complexes in solution is limited as they can undergo irreversible degradation reactions ((A. E. Martell, A. K. Basak, C. J. Raleigh, Pure Appl. Chem., 1988, 60, 1325-1329). Furthermore, these species cannot be deoxygenated simply by decreasing the dioxygen partial pressure. Immobilising the ligand on a solid matrix should facilitate use and limit degradation of the oxygenated species and improve the reversibility of the reaction.

Direct synthesis in a micellar medium of mesostructured silicas having large specific surface areas (800-1400 $m^2 \cdot g^{-1}$) with a very narrow pore distribution which is adjustable between 2 and 10 nm was discovered in 1992 (J. S. Beck, J. C. Vartuli, W. J. Roth, M. E. Leonowicz, C. T. Kresge, K. D. Schmitt, C. T. Chu, D. H. Olson, E. W. Sheppard, S. B. Higgins, J. L. Schlenker; J. Am. Chem. Soc. 1992, 114, 10834). This new family of mesoporous materials (MTS: abbreviation of the English term "micelle-templated silica"), is obtained from the cooperative assembly of an inorganic phase round an organic phase consisting of surfactants in a micellar concentration (J. Y. Ying, C. P. Mehnert, M. S. Wong; Angew. Chem. Int. Ed., 1999, 38, 56-77). Once the material has been formed, elimination of the surfactant liberates the porosity of the inorganic framework and thus leads to a porous organised inorganic phase.

BRIEF DESCRIPTION OF THE DRAWINGS

FIG. 1. Isotherm of adsorption of $O_2$ on one embodiment of the invention prepared from $Cl(CH_2)_3SiO_{1.5}$, 9 $SiO_2$, 5-azanonane-1,9-diamine, and $CuCl_2$ ($M_B$(7-Cu)) ($1^{st}$ Cycle);

FIG. 2. Isotherm of adsorption of $O_2$ on another embodiment of the invention prepared from $Cl(CH_2)_3SiO_{1.5}$, 9 $SiO_2$, 5,8-diazadodecane-1,12-diamine, and $CuCl_2$ ($M_B$(9-Cu)) ($1^{st}$ Cycle).

DESCRIPTION OF THE INVENTION

During his attempts to diversify his means of separating gases, the applicant has developed the novel process forming the subject of the present invention.

The invention relates to a process for preparing organic-inorganic hybrid materials with controlled porosity and functionality, comprising:

a stage (a) of hydrolysis and polycondensation of a mixture of at least one compound of formula (I):

$$Z\text{-}R_1\text{---}Si(OR)(OR')(OR'') \qquad (I)$$

in which:

Z represents either a halogen atom selected from chlorine, bromine or iodine atoms, or an amino or phosphino group;

R, R' and R", which may be the same or different, independently of each other represent an alkyl radical containing 1 to 4 carbon atoms, $R_1$ represents a divalent radical derived from a saturated or unsaturated aliphatic hydrocarbon chain containing 1 to 30 carbon atoms, in which there are optionally inserted one or more structural links selected from the arylene group or the —O—, —S—, —O—C(=O)—, —N($R_6$)—C(=O)— or —N($R_6$)— fragments, in which $R_6$ represents a hydrogen atom, an aliphatic hydrocarbon radical containing 1 to 6 carbon atoms, a benzyl radical or a phenethyl radical, said chain being unsubstituted or substituted by one or more radicals selected from the halogen atoms, the hydroxy group, alkyl radicals containing 1 to 4 carbon atoms or benzyl or phenethyl radicals;

with at least one alkali or alkaline-earth silicate (II) in a molar ratio (I)/(II)=1/9 in the presence of at least one nonionic surfactant in a micellar concentration to form a mesoporous silica represented by formula (III):

$$Z\text{-}R_1\text{---}SiO_{1.5}9SiO_2 \qquad (III),$$

said stage (a) being followed by a stage (b) of anchoring, on the mesoporous silica of formula (III), an equivalent of an organic compound represented by (Δ)N—H comprising at least one group —NH— capable of reacting with the function Z of said mesoporous silica to form the functionalised mesoporous silica represented by formula (IV):

$$(\Delta)N\text{---}R_1\text{---}SiO_{1.5}9SiO_2 \qquad (IV).$$

According to a first variation of the process as defined above, stage (b) is followed by a stage (c) of complexing of a metal cation by reacting the functionalised mesoporous silica represented by formula (IV) with a salt of said cation to form an organometallic complex (V).

In the process and the variation thereof as defined above, $R_1$ represents more particularly the divalent radical of formula ($R_{1a}$):

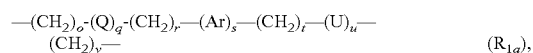

$$\text{---}(CH_2)_o\text{-}(Q)_q\text{-}(CH_2)_r\text{---}(Ar)_s\text{---}(CH_2)_t\text{---}(U)_u\text{---}$$
$$(CH_2)_v\text{---} \qquad (R_{1a}),$$

in which:

o, r, t and v, which may be the same or different, independently of one another represent an integer greater than or equal to 0 and lower than or equal to 6, Q and U, which may be the same or different, independently of one another represent an oxygen atom, a sulphur atom or one of the groups —O—C(=O)—, —C(=O)—O—, —NH—C(=O)—, —C(=O)—NH— or —NH—, q, s and u, which may be the same or different, independently of one another represent an integer greater than or equal to 0 and lower than or equal to 1, Ar represents an arylene radical and, in particular, a phenylene radical, with the proviso that:

when q is equal to 1, then o is different from 0,
when q is equal to 1 and u is equal to 0, then the sum r+s+t+v is different from 0,
when u is equal to 1, then v is different from 0,
when u is equal to 1 and q is equal to 0, then the sum o+r+s+t is different from 0,
when s is equal to 0 and q and u are each equal to 1, then the sum r+t is different from 0, and
the sum o+r+t+v is lower than or equal to 24.

$R_1$ represents quite particularly one of the divalent radicals —$(CH_2)_x$—, in which x is between 3 and 20 and is preferably between 3 and 6 inclusive or one of the radicals:

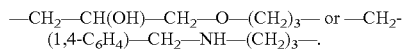

In the variation of the process as above, metallic cation mainly denotes the cations of transition metals, the cations of precious metals, the cations of lanthanides and the cations of actinides. The metallic cation is more particularly selected from the cations of iron, cobalt, europium, uranium, nickel, manganese, copper, chromium, zinc, silver, cadmium, lead, mercury, gold, platinum, palladium, uranium, cerium or gadolinium.

In the variation of the process as above, the salt of metallic cation is more particularly selected from the chloride, bromide, iodide, fluoride, tetrafluoroborate, sulphate or nitrate of said cation.

Compounds Δ (NH) which may be used in the process and the variation thereof as defined above include, for example, the cyclic compounds such as polyazacycloalkanes, the porphyrin derivatives or the aliphatic polyamines.

Suitable polyazacycloalkanes include more particularly the triazacycloalkanes, such as 1,4,7-triazacyclononane, 1,4,8-triazacyclodecane or 1,5,9-triazacyclododecane, the tetraazacycloalkanes such as 1,4,7,10-tetraazacyclododecane (cyclene), 1,4,7,10 tetraazacyclotridecane, 1,4,7,11-tetraazacyclotetradecane, 1,4,8,11-tetraazacyclotetradecane (or cyclam), 1,4,8-trimethyl 1,4,8,11-tetraazacyclotetradecane, 1,4,8,12-tetraazacyclopentadecane, 1,5,9,13-tetraazacyclohexadecane 1,5,10,14-tetraazacyclooctadecane, 1-methyl 1,4,8,11-tetraazacyclotetradecane, 6-dodecyl 1,4,8,11-tetraazacyclotetradecane, 3-dodecyl 1,5,9,13-tetraazacyclohexadecane, 3-dodecyl 1,5,10,14-tetraazacyclooctadecane, 5,5,7,12,12,14-hexamethyl 1,4,8,11-tetraazacyclotetradecane, 1-benzyl 1,4,8,11-tetraazacyclotetradecane, 1-[(2-pyridyl)methyl] 1,4,8,11-tetraazacyclotetradecane, 1-[(3-pyridyl)methyl] 1,4,8,11-tetraazacyclotetradecane or 1,4-dibenzyl 1,4,8,11-tetraazacyclotetradecane, the pentaazacycloalkanes such as 1,4,7,10,13-pentaazacyclopentadecane, 4,7,11,15-pentaazacyclooctadecane, 1,5,9,13,17-pentaazacyclooctadecane or 1,4,7,10-tetraethyl 1,4,7,10,13-pentaazacyclopentadecane, the hexaazacycloalkanes such as 1,4,7,10,13,16-hexaazacyclooctadecane, 1,5,9,13,17,20-hexaazacyclotetracosane or 1,4,7,10,13-pentaethyl 1,4,7,10,13,16 hexaazacyclooctadecane, the octaazacycloalkanes such as 1,4,8,11,15,18,22,25-octaazacyclooctacosane, 6,6,13,13,20,20,27,27-octamethyl 1,4,8,11,15,18,22,25-octaazacyclooctacosane, 6,6,13,13,20,20,27,27-octamethyl 1,4,8,11,15,18,22,25-octaazacyclooctacosane, 1,4,8,11,15,18,22,25-octaazacyclooctacosane, 6,6,13,13,20,20,27,27-octamethyl 1,4,8,11,15,18,22,25-octaazacyclooctacosane or 6,6,13,13,20,20,27,27-octamethyl 1,4,8,11,15,18,22,25-octaazacyclooctacosane-2,3,16,17-tetraone, the hexadecaazacycloalkanes such as 1,4,8,11,15,18,22,25,29,32,36,39,43,46,50,53-hexadecaazacyclohexapentacontane, 1,4,7,10,13,16,19,22,25,28,31,34,37,40,43,46-hexadecaazacyclooctatetracontane, 1,4,7,10,13,16,19,22,25,28,31,34,37,40,43,46-hexadecaazacyclooctatetracontane-2,3,14,15,26,27,38,39-octaone, 1,4,8,11,15,18,22,25,29,32,36,39,43,46,50,53-hexadecaazacyclohexapentacontane-2,3,16,17,30,31,44,45-octaone or 1,4,7,10,13,16,19,22,25,28,31,34,37,40,43,46-hexadecaazacyclooctatetracontane-2,3,14,15,26,27,38,39-octaone.

Suitable porphyrin derivatives include, for example: [4-(2,8,13,17-tetraethyl-3,7,12,18-tetramethyl-porphyrin-5-yl) phenylamine], [4-(2,8,13,17-tetraethyl-3,7,12,18-tetramethyl-porphyrin-5-yl)benzylamine], [4-(15-phenyl-porphyrin-5-yl)-phenylamine], [4-(15-phenyl-porphyrin-5-yl)-benzylamine], [4-(10,15,20-triphenyl-porphyrin-5-yl)-phenylamine], or [4-(10,15,20-triphenyl-porphyrin-5-yl)-benzylamine].

Suitable acyclic compounds include, for example, the aliphatic polyamines and more particularly the triazaalkanes such as 4-azaheptane-1,7-diamine, 4-azaoctane-1,8-diamine or 5-azanonane-1,9-diamine, the tetraazaalkanes such as 4,7-diazadecane-1,10-diamine, 4,8-diazaundecane-1,11-diamine, 5,9-diazadodecane-1,12-diamine, 5,8-diazadodecane-1,12-diamine, 4,8,diazadodecane-1,12-diamine, 5,9-diazamidecane-1,13-diamine, 5,10-diazatetradecane-1,14-diamine, 6,10-diazapentadecane 1,15-diamine, the pentaazaalkanes such as 1,4,7-triazamidecane 1,13-diamine, 4,8,12-triazahexadecane-1,16-diamine or 5,8,11-triazapentadecane-1,15-diamine or else the hexaazaalkanes such as 4,7,10,13-tetraazahexadecane-1,16-diamine or 5,9,13,17-tetraazaeicosane-1,20-diamine.

According to a further aspect, the present invention relates to functionalised mesoporous silica represented by formula (IV) as defined hereinbefore, and to the metal complex (V) obtainable by reacting said compound of formula (IV) with a metallic cation salt as defined hereinbefore.

According to a last aspect, the present invention relates to the use of these metallated materials, as defined hereinbefore, to separate a predetermined gas from a mixture of gases. It involves bringing said mixture of gases into contact with one of the metallated hybrid gels as defined hereinbefore under conditions which allow absorption of said gas to be separated followed by desorption of said gas fixed on the solid then recovery of said desorbed gas. This use is preferably applied to the separation of oxygen from the air, either to produce pure oxygen or to remove the oxygen from the air.

Given the complexing capacity of these ligands with respect to the transition metal salts and the salts of lanthanides, the method of complexing is general to all the aforementioned metal salts and the materials thus prepared are advantageously used in heterogeneous catalysis, for the depollution of effluents, for the purification, activation and storage of gases, for obtaining photoluminescent materials and materials having magnetic or electrical properties.

EXAMPLES

The following examples illustrate the invention without limiting it.

I—Preparation of Mesoporous Materials a—Principle of the Method

The process the subject of the present invention comprises the hydrolysis and polycondensation of a mixture of (3-chloropropyl) trimethoxysilane and sodium silicate in a proportion of 1/9 in the presence of nonionic surfactants such as TERGITOL™ 15S12 [$CH_3(CH_2)_{14}$—($OCH_2CH_2$)$_{12}$—$OH$] or the block copolymer $EO_{20}PO_{70}EO_{20}$ (PLURONIC™ P. 123).

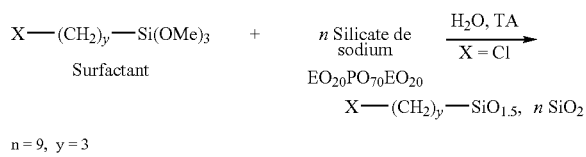

n = 9, y = 3

The milky emulsion containing the surfactant mixture, the (3-chloropropyl) trimethoxy silane and the sodium silicate is transformed into a microemulsion, while bringing the pH of the solution to 3, by addition of an aqueous hydrochloric acid solution and heating the mixture slightly until the solution is perfectly clear. Sodium fluoride is then added and causes precipitation of the solid containing the surfactant. The surfactant is eliminated by extraction of the ethanol with reflux.

In the following account, the materials are designated in the following manner: $M_A$ indicates that the material has been prepared with TERGITOL™ 15S12 and $M_B$ indicates that the material has been prepared with the block copolymer $EO_{20}PO_{70}EO_{20}$. This index letter is followed by the name of the functional grouping between brackets. The two materials described hereinbefore will therefore be denoted $M_A(Cl)$ and $M_B(Cl)$.

b—Examples of Preparation

1. Preparation of

A surfactant solution is prepared by mixing 2.0 g (0.34 mmol) of block copolymer $EO_{20}PO_{70}EO_{20}$, 70 cm³ of water and 1 cm³ of a sulphuric acid solution (4N). The solution is stirred until the surfactant has completely dissolved (about 1 hour). 0.9 g (4.5 mmol) of (3-chloropropyl) trimethoxy silane are added to this transparent solution. The resultant mixture is stirred for 5 minutes at ambient temperature. The formation of a transparent solution is then observed. This new solution is poured over a mixture of 59 cm³ of an aqueous sodium silicate solution containing 4.1% of $SiO_2$ and 1.5 cm³ of pure sulphuric acid. A white precipitate forms immediately. The reaction mixture is heated under reflux for 3 days. After filtration, the solid obtained is washed in water (2×100 cm³). The surfactant is then completely eliminated from the solid by extraction with 95% ethanol at reflux for 24 hours using a soxhlet. On completion of extraction, the solid is filtered then washed (2×20 cm³ of ethanol, then 2×20 cm³ of acetone and 2×20 cm³ of ether). After drying under vacuum at 120° C. for 12 hours, the hybrid material is obtained quantitatively (3.18 g) in the form of a white powder.

Analysis: Calculated Si/Cl: 10; found Si/Cl: 12.7.

The measurements of adsorption-desorption of the nitrogen at 77 K, taken on the solid obtained, demonstrate its mesoporous character, with a mean pore diameter (dp) equal to 65 Å ($10^{-10}$ m) and a BET specific surface area of 650 m²/g.

The X-ray powder diagram comprises a diffraction peak [a=107 Å ($10^{-10}$ m)] corresponding to the plane "$d_{100}$" which does not exist on the solid prepared in the absence of surfactant.

II—Anchorage of Polyazamacrocycles a—Principle

Starting with materials comprising chlorofunctional groups, it is possible to anchor a large number of chelating molecules such as the polyazamacrocycles within the pores. A single equivalent of cyclam is sufficient to provide quantitative anchoring:

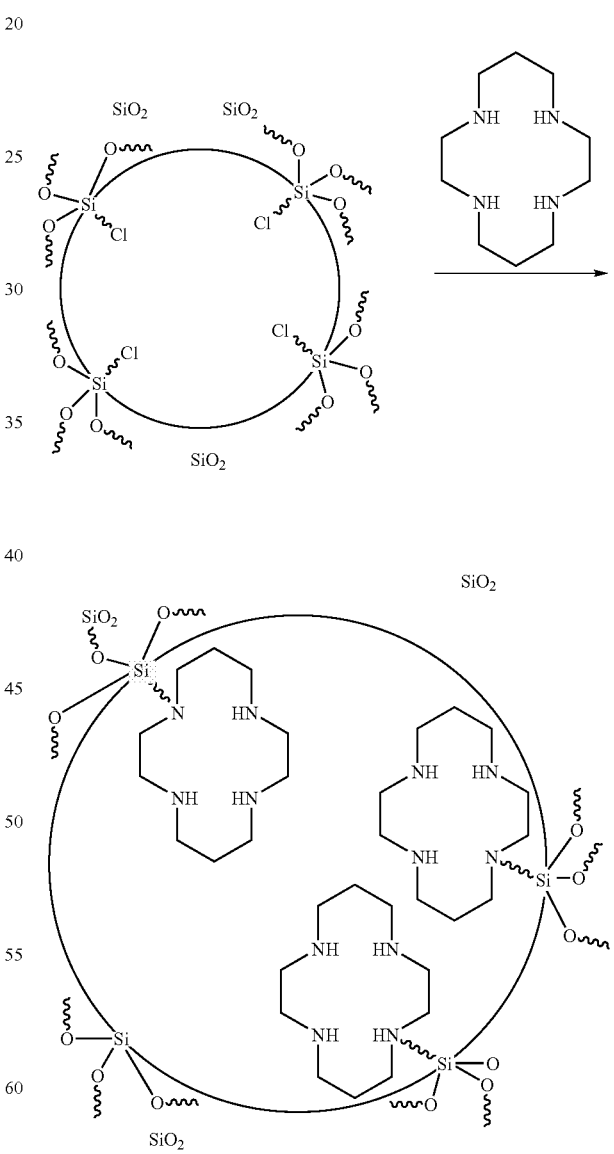

The method can be generalised to any chelating ligands carrying at least one nitrogen atom capable of reacting with the chloro function. It may advantageously be applied to the ligands mentioned above in the description, whether they are polyazacycloalkanes, porphyrins or aliphatic polyamines.

b—Examples of Anchorage

1—Anchorage of Cyclam on $M_B(Cl)$ [$M_B(cycl)$]

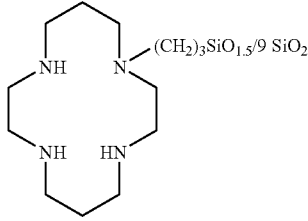

0.626 g of cyclam (3.13 mmol) and 125 cm³ of acetonitrile are brought to reflux in a 500 cm³ flask. After approx 30 minutes at reflux, a large proportion of the cyclam is solubilised. 0.678 g of triethylamine and 1.5 g of $M_B(Cl)$, prepared as described in the foregoing paragraph 1, is then added and the mixture is left at reflux for 48 hours. The hybrid solid is then recovered by filtration of the hot solution so as to avoid precipitation of the excess cyclam, then taken up in the hot chloroform 3 times for 5 minutes while stirring (3×30 cm³) then 5 times with 30 cm³ of hot methanol. The desired product is obtained after washing with acetone and ether and oven drying under vacuum for 12 h at 120° C.

Conductometric analysis of the excess cyclam using a titrated solution of $CuBr_2$ shows that 100% of the cyclam is anchored.

$S_{BET}$=660 m²·g⁻¹; dp=63 Å; RX, a=107 Å.

2—Anchorage of 5-azanonane-1,9-diamine on $M_B(Cl)$ [$M_B(cycl)$]

40 cm³ of acetonitrile, 0.5 g of $M_B(Cl)$, 2 equivalents of triethylamine and 10 equivalents of 5-azanonane-1,9-diamine are introduced into a 100 cm³ flask. The reaction mix is refluxed for 5 hours then the solid is filtered over sintered material No. 3 and washed 3 times with 20 cm³ of ethanol and once with 10 cm³ of ether. The desired product $M_B(7)$ is obtained after drying for 12 hours at 120° C. under a pressure of 10 mm of mercury. The results of elemental analysis show that it contains 0.77 mmol·g⁻¹ of grafted triamine.

|  | C % | H % | N % |
|---|---|---|---|
| calculated | 14.1 | 2.88 | 5.49 |
| found | 11.92 | 3.41 | 3.22 |

$S_{BET}$=259 m²·g⁻¹, dp=59 Å.

3—Anchorage of 5,8-diazadodecane-1,12-diamine on $M_B(Cl)$ [$M_B(9)$]

The material $M_B(9)$ is obtained by the same mode of operation as the material $M_B(7)$, starting with 0.5 g of $M_B(Cl)$ and 5,8-diazadodecane-1,12-diamine. The results of elemental analysis show that it contains 0.68 mmol·g⁻¹ of grafted tetraamine.

|  | C % | H % | N % |
|---|---|---|---|
| calculated | 16.36 | 3.35 | 6.94 |
| found | 13.40 | 3.14 | 3.82 |

$S_{BET}$=133 m²·g⁻¹, dp=66 Å.

III—Complexing of Metal Salts

1—Complexing of $CuCl_2$ on the material $M_B(cycl)$ [$M_B(cycl-Cu)$]

1 g of the material $M_B(cycl)$ (1.2 mmol) is placed under argon in a 70 cm³ Schlenk flask. 20 cm³ of anhydrous ethanol are added thereto. 228 mg of copper chloride ($CuCl_2$) (1.4 equivalents of salt per cyclam) are dissolved in 40 cm³ of anhydrous ethanol in a second 70 cm³ Schlenk. This solution is poured over the suspension of solid in ethanol. The reaction mix is left to reflux for 24 hours. The solid is then filtered under argon, washed 3 times with 20 cm³ of ethanol, 3 times with 20 cm³ of acetone then with 3 times 20 cm³ of anhydrous ether.

Conductometric analysis of the copper chloride remaining in the filtrate by a titrated solution of cyclam shows that complexing is 88% complete.

$S_{BET}$=515 m²·g⁻¹; dp=44 Å.

2—Complexing of $CuCl_2$ on the Material $M_B(7)$ [$M_B(7-Cu)$]

0.3 g of $M_B(7)$, 2 equivalents of $CuCl_2$, $2H_2O$ and 20 cm³ of ethanol are introduced into a 100 cm³ flask. The reaction mix is left for 12 hours at ambient temperature with stirring. It is then filtered in air. The solid obtained is washed 3 times with 10 cm³ of ethanol then dried under a pressure of 3 torr for 1 h at ambient temperature.

Analysis of the copper by X-ray fluorescence shows that the compound obtained contains 0.377 mmol·g⁻¹ of copper.

$S_{BET}$=230 m²·g⁻¹; dp=58 Å.

3—Complexing of $CuCl_2$ on the Material $M_B(9)$ [$M_B(9-Cu)$]

Complexing of $CuCl_2$ on the material $M_B(9)$ was carried out using the same mode of operation as for the complexing of $CuCl_2$ on $M_B(7)$.

Analysis of the copper by X-ray fluorescence shows that the compound obtained contains 0.410 mmol·g⁻¹ of copper.

$S_{BET}$=119 m²·g⁻¹; dp=64 Å.

IV—Fixing of the Oxygen on the Complex

Measurements of adsorption of $O_2$ by the materials $M_B(7\text{-}Cu)$ and $M_B(9\text{-}Cu)$ were taken at 21° C. using a MICROMERITICS ASAP™ 2010 apparatus. The experimental data obtained was processed by a non-linear adjustment, according to Langmuir's Law: $V=V_m KP/(1+KP)$. In all cases, the results indicate the need to use 1 isotherm of the Langmuir type to take account of the phenomenon of chemisorption and 1 isotherm of the Henry type to take account of physisorption.

The fixing of oxygen on the materials $M_B(7\text{-}Cu)$ and $M_B(9\text{-}Cu)$ is described by way of example. The solids were degassed for 12 h at 120° C. under 10⁻³ torr prior to adsorption of the nitrogen or oxygen. The results are reported in the table hereinafter and the isotherms of adsorption of the oxygen on these materials appear in FIGS. 1 and 2.

This table shows that the material $M_B$(7-Cu) has an exceptional affinity for oxygen since, on the one hand, the partial dioxygen pressure $(PO_2)_{1/2}$ is very weak and, on the other hand, the fixing of dioxygen is reversible.

| Solid | cycle | $Vo_2$ (cm$^3 \cdot$g$^{-1}$) | $Vn_2$ (cm$^3 \cdot$g$^{-1}$) | $(Po_2)_{1/2}$ torr | Yield % (oxygenation) |
|---|---|---|---|---|---|
| $M_B$ (7-Cu) | 1 | 2.1 | 0.94 | 0.37 | 21 |
|  | 2 | 2.2 |  | 0.51 | 22 |
| $M_B$ (9-Cu) | 1 | 1.96 | 0.37 | 3.78 | 22 |

The invention claimed is:

1. A method for separating a predetermined gas from a mixture of gases, said method comprising a step of contacting an organometallic complex with said mixture of gases, said complex being obtained by reacting a salt of a metallic cation with a compound having the following formula:

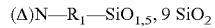

$(\Delta)N-R_1-SiO_{1.5}, 9\ SiO_2$ in which $R_1$ represents a divalent radical derived from a saturated or unsaturated aliphatic hydrocarbon chain containing 1 to 30 carbon atoms, in which there are optionally inserted one or more structural links selected from an arylene group or —O—, —S—, —O—C(=O)—, —N(R$_6$)—C(=O)—or —N(R$_6$)— fragments, in which R$_6$ represents a hydrogen atom, an aliphatic hydrocarbon radical containing 1 to 6 carbon atoms, a benzyl radical or a phenethyl radical, said chain being unsubstituted or substituted by one or more radicals selected from halogen atoms, a hydroxy group, alkyl radicals containing 1 to 4 carbon atoms or benzyl or phenethyl radicals, and $(\Delta)N$— represents the monovalent amine radical, derived from an organic compound comprising at least one —NH— group.

2. The method of claim 1, applied to the separation of oxygen from air, for either producing pure oxygen or removing oxygen from the air.

3. A method for the depollution of effluents, comprising a step of contacting said effluents with an organometallic complex, said complex being obtained by reacting a salt of a metallic cation with a compound having the following formula:

$(\Delta)N-R_1-SiO_{1.5}, 9\ SiO_2$ in which $R_1$ represents a divalent radical derived from a saturated or unsaturated aliphatic hydrocarbon chain containing 1 to 30 carbon atoms, in which there are optionally inserted one or more structural links selected from an arylene group or —O—, —S—, —O—C(=O)—, —N(R$_6$)—C(=O)— or —N(R$_6$)— fragments, in which R$_6$ represents a hydrogen atom, an aliphatic hydrocarbon radical containing 1 to 6 carbon atoms, a benzyl radical or a phenethyl radical, said chain being unsubstituted or substituted by one or more radicals selected from halogen atoms, a hydroxy group, alkyl radicals containing 1 to 4 carbon atoms or benzyl or phenethyl radicals, and $(\Delta)N$— represents the monovalent amine radical, derived from an organic compound comprising at least one —NH— group.

4. A method for the purification, activation and storage of gases, said method comprising a step of contacting said gases with an organometallic complex, said complex being obtained by reacting a salt of a metallic cation with a compound having the following formula:

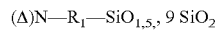

$(\Delta)N-R_1-SiO_{1.5}, 9\ SiO_2$ in which $R_1$ represents a divalent radical derived from a saturated or unsaturated aliphatic hydrocarbon chain containing 1 to 30 carbon atoms, in which there are optionally inserted one or more structural links selected from an arylene group or —O—, —S—, —O—C(=O)—, —N(R$_6$)—C(=O)— or —N(R$_6$)— fragments, in which R$_6$ represents a hydrogen atom, an aliphatic hydrocarbon radical containing 1 to 6 carbon atoms, a benzyl radical or a phenethyl radical, said chain being unsubstituted or substituted by one or more radicals selected from halogen atoms, a hydroxy group, alkyl radicals containing 1 to 4 carbon atoms or benzyl or phenethyl radicals, and $(\Delta)N$— represents the monovalent amine radical, derived from an organic compound comprising at least one —NH— group.

5. A method for obtaining photoluminescent materials and materials having magnetic or electrical properties, said method comprising a step of contacting said materials with an organometallic complex, said complex being obtained by reacting a salt of a metallic cation with a compound having the following formula:

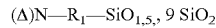

$(\Delta)N-R_1-SiO_{1.5}, 9\ SiO_2$ in which $R_1$ represents a divalent radical derived from a saturated or unsaturated aliphatic hydrocarbon chain containing 1 to 30 carbon atoms, in which there are optionally inserted one or more structural links selected from an arylene group or —O—, —S, —O—C(=O)—, —N(R$_6$)—C(=O)— or —N(R$_6$)— fragments, in which R$_6$ represents a hydrogen atom, an aliphatic hydrocarbon radical containing 1 to 6 carbon atoms, a benzyl radical or a phenethyl radical, said chain being unsubstituted or substituted by one or more radicals selected from halogen atoms, a hydroxy group, alkyl radicals containing 1 to 4 carbon atoms or benzyl or phenethyl radicals, and $(\Delta)N$— represents the monovalent amine radical, derived from an organic compound comprising at least one —NH— group.

6. Catalyst for heterogeneous catalysis consisting of an organometallic complex, said complex being obtained by reacting a salt of a metallic cation with a compound having the following formula:

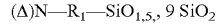

$(\Delta)N-R_1-SiO_{1.5}, 9\ SiO_2$ in which $R_1$ represents a divalent radical derived from a saturated or unsaturated aliphatic hydrocarbon chain containing 1 to 30 carbon atoms, in which there are optionally inserted one or more structural links selected from an arylene group or —O—, —S, —O—C(=O)—, —N(R$_6$)—C(=O)— or —N(R$_6$)— fragments, in which R$_6$ represents a hydrogen atom, an aliphatic hydrocarbon radical containing 1 to 6 carbon atoms, a benzyl radical or a phenethyl radical, said chain being unsubstituted or substituted by one or more radicals selected from halogen atoms, a hydroxy group, alkyl radicals containing 1 to 4 carbon atoms or benzyl or phenethyl radicals, and $(\Delta)N$— represents the monovalent amine radical, derived from an organic compound comprising at least one —NH— group.

\* \* \* \* \*